United States Patent [19]

Bloom et al.

[11] 4,259,498

[45] Mar. 31, 1981

[54] PROCESS FOR PREPARING BENZISOTHIAZOLE-1,1-DIOXIDE AND NAPHTHO-1,2-THIAZINE-1,1-DIOXIDE COMPOUNDS

[75] Inventors: Stanley M. Bloom, Waban; Alan L. Borror, Lexington; James W. Foley, Andover, all of Mass.

[73] Assignee: Polaroid Corporation, Cambridge, Mass.

[21] Appl. No.: 84,251

[22] Filed: Oct. 12, 1979

Related U.S. Application Data

[62] Division of Ser. No. 836,004, Sep. 23, 1977, Pat. No. 4,191,689.

[51] Int. Cl.³ .......................................... C07D 275/04
[52] U.S. Cl. ................................... 548/207; 548/208
[58] Field of Search ................ 544/33; 548/209, 207, 548/208

[56] References Cited

PUBLICATIONS

Mustafa et al., J. Chem. Soc., 1953, p. 1339–1340.
Abramovitch et al., J. Chem. Soc., "Perkin Trans. I", vol. 22, 1974, pp. 2589–2594.
Dutt, S., J. Chem. Soc., 121, 1922, pp. 2389–2394.
McOmie, J., "Protective Groups in Organic Chemistry", Plenum Press, N.Y., 1973, Chap. 4.

*Primary Examiner*—Nicholas S. Rizzo
*Attorney, Agent, or Firm*—Sybil A. Campbell

[57] ABSTRACT

This invention relates to certain 3,3,-di(4'-OP-carbocyclic aryl)-2,3-dihydrobenz[d]isothiazole-1,1-dioxides (and-2,3-dihydronaphtho[1,8-de]-1,2-thiazine-1,1-dioxides) and to the preparation thereof by reacting (a) at least 2 equivalents of (i) a 4'-OP-carbocyclic aryllithium compound wherein P is a protecting group compatible with organometallic reagents or (ii) a 4'-OP-carbocyclic arylMgE compound wherein P is a protecting group compatible with organometallic reagents and E is chloro, bromo or iodo and (b) 1 equivalent of a compound selected from a 3-chlorobenz[d]isothiazole-1,1-dioxide and a 3-chloronaphtho[1,8-de]-1,2-thiazine-1,1-dioxide to give the corresponding 3,3-di(4'-OP-carbocyclic aryl)-2,3-dihydrobenz[d]isothiazole-1,1-dioxide or the corresponding 3,3-di(4'-OP-carbocyclic aryl)-2,3-dihydronaphtho[1,8-de]-1,2-thiazine-1,1-dioxide, which compounds are useful in the synthesis of phenol and 1-naphthol sulfam(na)-phthaleins employed, for example, as photographic optical filter agents and filter agent precursors.

18 Claims, No Drawings

PROCESS FOR PREPARING BENZISOTHIAZOLE-1,1-DIOXIDE AND NAPHTHO-1,2-THIAZINE-1,1-DIOXIDE COMPOUNDS

This is a division of application Ser. No. 836,004, filed Sept. 23, 1977, now U.S. Pat. No. 4,191,689.

BACKGROUND OF THE INVENTION

1. Field of the Invention

This invention relates to certain 3,3-disubstituted-2,3-dihydrobenz[d]isothiazole-1,1-dioxides and to certain 3,3-disubstituted-2,3-dihydronaphtho[1,8-de]-1,2-thiazine-1,1-dioxides useful in the preparation of phenol and 1-naphthol sulfamphthaleins and sulfamnaphthaleins and to the preparation of said 3,3-disubstituted compounds.

2. Description of the Prior Art

Various procedures have been reported for synthesizing 3-disubstituted-benz[d]isothiazole-1,1-dioxides and 3,3-disubstituted-2,3-dihydrobenz[d]isothiazole-1,1-dioxides from saccharin (3-oxo-2,3-dihydrobenz[d]isothiazole-1,1-dioxide) and from saccharin pseudo-chloride (3-chlorobenz[d]isothiazole-1,1-dioxide). As reported by A. Mustafa et al, *J. Chem. Soc.*, 1952, p. 1339, the treatment of saccharin pseudo-chloride with excess phenylmagnesium bromide gave the corresponding 3,3-diphenyl-2,3-dihydrobenz[d]isothiazole-1,1-dioxide in almost quatitative yield. Methyl-, ethyl-, n-propyl- and n-butylmagnesium halides were reported by these authors to react analogously. R. A. Abramovitch et al, *J. Chem. Soc., Perkin Trans I*, 1974(22), p. 2589, reviewed and reinvestigated the reactions of saccharins with alkyl and aryl Grignard reagents and found that either the 3-alkyl (or 3-aryl)-benz[d]isothiazole-1,1-dioxide and/or the open-chain tertiary alcohol, o—CR$_2$OH benzenesulfonamide wherein R is alkyl (or aryl) were obtained with one exception. When saccharin was treated with an excess of phenylmagnesium bromide in boiling tetrahydrofuran, 3,3-diphenyl-2,3-dihydrobenz[d]isothiazole-1,1-dioxide was obtained as the minor product together with the open-chain tertiary alcohol.

R. A. Abramovitch et al also investigated the reaction of saccharin and saccharin pseudo-chloride with organolithium compounds and found that the reaction of saccharin with alkyl- and aryllithium compounds, such as, n-butyllithium and p-methoxyphenyllithium in tetrahydrofuran at −78° C. gave the corresponding 3-substituted-benz[d]isothiazole-1,1-dioxide, exclusively. In addition to this general method for synthesizing 3-alkyl (or 3-aryl)-benz[d]isothiazole-1,1-dioxides, the authors reported that the reaction of the pseudo-chloride with organolithium compounds, such as, n-butyllithium in tetrahydrofuran at −78° C. gave the corresponding 3,3-disubstituted-2,3-dihydrobenz[d]isothiazole-1,1-dioxide as the major product.

Besides the reactions with Grignard and organolithium reagents, Friedel-Crafts reactions with the saccharins also have been disclosed. Dutt, *J. Chem. Soc.*, 121, p. 2389 (1922) reported the condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins". Though the structure of 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali and also, that the compound corresponding to the structure given could not be synthesized by repeating the procedures reported by Dutt.

Copending U.S. patent application Ser. No. 836,010 of Stanley M. Bloom, Alan L. Borror and James W. Foley filed concurrently herewith is directed to a method of synthesizing phenol and 1-naphthol sulfamphthaleins and sulfamnaphthaleins possessing a carbonyl group in the 2-position of the sulfam(na)phthalein ring. Depending upon the carbonyl group and the phenolic and/or naphtholic substituents, the products of the synthesis may be employed as pH-sensitive indicator dyes, antihalo dyes or photographic optical filter agents. As disclosed and claimed therein, the method of preparing these compounds comprises reacting a 3-(4'-OP-carbocyclic aryl)-3-(carbocyclic aryl)-2,3-dihydrobenz[d]isothiazole-1,1-dioxide (or -2,3-dihydronaphtho[1,8-de]-1,2-thiazine-1,1-dioxide) wherein P is a protecting group with a carboxylic acid halide to yield the corresponding 2-carbonyl derivative followed by removing the protecting group with weak acid to yield the product. In the compounds prepared by this method, one of the 3,3 substituents is a 4'-hydroxycarbocyclic aryl moiety and the other may be the same or different.

The present invention is concerned with 3,3-di(4'-OP-carbocyclic aryl)-2,3-dihydrobenz[d]isothiazole-1,1-dioxides (and -2,3-dihydronaphtho[1,8-de]-1,2-thiazine-1,1-dioxides) useful as starting materials in the aforementioned synthesis and to the preparation of said isothiazole and said 1,2-thiazine-1,1-dioxides.

SUMMARY OF THE INVENTION

It is, therefore, the primary object of the present invention to provide certain 3,3-disubstituted-2,3-dihydrobenz[d]isothiazole-1,1-dioxides and certain 3,3-disubstituted-2,3-dihydronaphtho[1,8-de]-1,2-thiazine-1,1-dioxides useful in the preparation of phenol and 1-naphthol sulfam(na)phthaleins.

It is another object of the present invention to provide a method of preparing said 3,3-disubstituted isothiazole and 1,2-thiazine-1,1-dioxides.

Other objects of this invention will in part be obvious and will in part appear hereinafter.

This invention accordingly comprises the process involving the several steps and the relation and order of one or more of such steps with respect to each of the others and the product possessing the features, properties and the relation of elements which are exemplified in the following detailed disclosure and the scope of the application of which will be indicated in the claims.

According to the present invention, 3,3-di(4'-OP-carbocyclic aryl)-2,3-dihydrobenz[d]isothiazole-1,1-dioxides are prepared by reacting (a) at least two equivalents of an OP-carbocyclic aryl compound wherein P is a protecting group as a lithium or Grignard reagent with one equivalent of saccharin pseudo-chloride to give the corresponding 3,3-di-(4'-OP-carbocyclic aryl)-2,3-dihydrobenz[d]isothiazole-1,1-dioxide. The 1,2-thiazine-1,1-dioxides are prepared in the same manner except that 3-chloronaphtho[1,8-de]-1,2-thiazine-1,1-dioxide is reacted with the OP-carbocyclic aryl compound.

The subject method is applicable to the synthesis of 3,3-disubstituted-2,3-dihydrobenz[d]isothiazole-1,1-dioxides and 3,3-disubstituted-2,3-dihydronaphtho[1,8-de]-1,2-thiazine-1,1-dioxides wherein the 3,3 substituents, the same, are 4'-OP-phenyl moieties, unsubstituted or substituted with one or more groups compatible with organometallic reagents, or 4'-OP-naphthyl moieties, unsubstituted or substituted with one or more groups compatible with organometallic reagents. Such compounds wherein the 3,3 substituents are different, e.g., one is a 4'-OP-phenyl moiety and the other of the 3,3 substituents is a 4'-OP-naphthyl moiety comprise the subject matter of copending U.S. patent application Ser. No. 836,008 of Alan L. Borror, Louis Cincotta, James W. Foley and Marcis M. Kampe filed concurrently herewith.

For a fuller understanding of the nature and objects of the present invention, reference should be had to the following detailed description.

DESCRIPTION OF THE PREFERRED EMBODIMENTS

Specifically, the method of the present invention comprises reacting (a) at least 2 equivalents of (i) a 4'-OP-carbocyclic aryllithium compound wherein P is a protecting group selected from 4'-OP-phenyllithium, unsubstituted or substituted with one or more substituents compatible with organometallic reagents, the same or different, and 4'-OP-naphthyllithium, unsubstituted or substituted with one or more substituents compatible with organometallic reagents, the same or different, or (ii) a 4'-OP-carbocyclic arylMgE compound wherein P is a protecting group and E is chloro, bromo or iodo selected from 4'-OP-phenylMgE, unsubstituted or substituted with one or more substituents compatible with organometallic reagents, the same or different, and 4'-OP-naphthylMgE, unsubstituted or substituted with one or more substituents compatible with organometallic reagents, the same or different, and (b) a compound selected from a 3-chlorobenz[d]isothiazole-1,1-dioxide and a 3-chloronaphtho[1,8-de]-1,2-thiazine-1,1-dioxide in an inert organic solvent to give (c) the compound having the formula

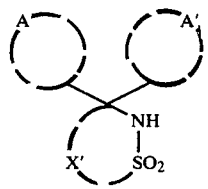

wherein said A' moieties, the same, each represent a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; P is a protecting group; and X' represents the atoms necessary to complete a 2,3-dihydrobenz[d]isothiazole-1,1-dioxide moiety or a 2,3-dihydronaphtho[1,8-de]-1,2-thiazine-1,1-dioxide moiety.

The above reaction scheme is illustrated below using as specific reactants, the lithium or Grignard reagent of phenol blocked with a protecting group, P, and 3-chlorobenz-[d]isothiazole-1,1-dioxide (saccharin pseudo-chloride).

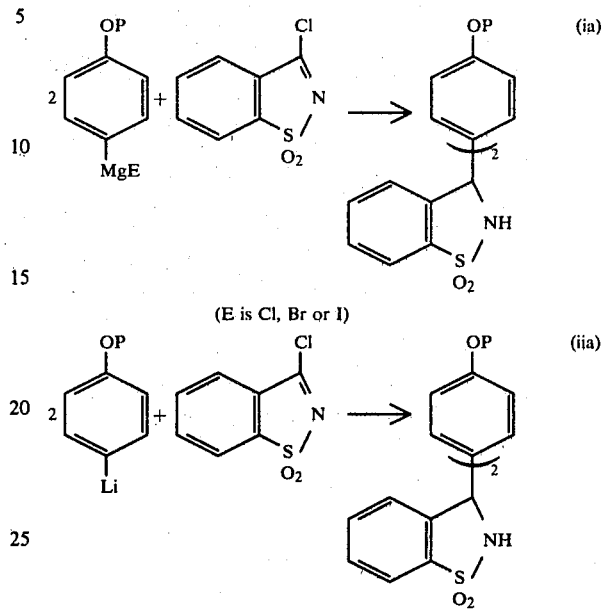

The substituents selected for the A' moieties and, if desired, for the sulfam(na)phthalein moiety should be stable to organometallic reagents, such as, lithium and Grignard reagents and include substituents capable of being blocked during the synthesis by a protecting group that can be subsequently removed under weakly acid conditions simultaneously with the protecting group P used to block the functional —OH.

As indicated above, the sulfam(na)phthaleins produced in accordance with the subject method are symmetrical, i.e., sulfam(na)phthaleins wherein the 3,3 substituents are identical.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

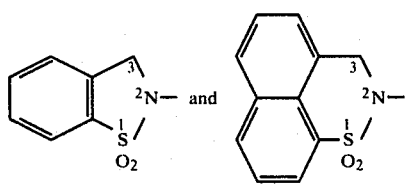

Typical of the sulfam(na)phthaleins that may be prepared according to the present invention are those represented by the following formula:

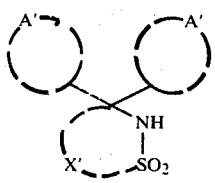

wherein said A' moieties, the same, each represent a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; P is a protecting group; and X' represents the atoms necessary to complete a 2,3-dihydrobenz[d]isothiazole-1,1-dioxide moiety or a 2,3-dihydronaphtho[1,8-de]-1,2-thiazine-1,1-dioxide moiety.

Typical substituents compatible with or capable of being protected to be compatible with organometallic reagents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenylhexyl and phenyldodecyl; alkoxy, such as, methoxy, ethoxy, butoxy, octadecyloxy, 1-ethoxy-2-($\beta$-ethoxyethoxy); aryloxy, such as, phenoxy, benzyloxy and naphthoxy; alkoxyalkyl, such as, methoxymethyl, ethoxymethyl and dodecyloxyethyl; halo, such as, fluoro, bromo and chloro; trihalomethyl, such as, trifluoromethyl and trichloromethyl; sulfonamido (—NH—SO$_2$R° wherein R° is alkyl, aryl, alkaryl or aralkyl); sulfamoyl (—SO$_2$—NH—R° wherein R° has the same meaning given above);

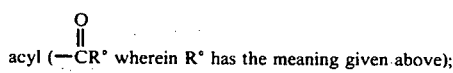

acyl (—CR° wherein R° has the meaning given above);

sulfonyl (—SO$_2$—R° wherein R° has the same meaning given above); sulfo; cyano, carboxy, hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino).

In a preferred embodiment, the method of the present invention comprises reacting (a) at least 2 molar equivalents of a compound having the formula

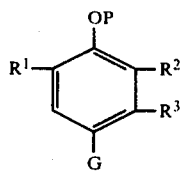

wherein G is Li, MgCl, MgBr or MgI; P is a protecting group; R$^1$ and R$^2$ each are selected from hydrogen, alkyl, alkoxy, chloro and fluoro; R$^3$ is hydrogen, alkyl, alkoxy or —OP; and R$^2$ and R$^3$ taken together represent the carbon atoms necessary to complete a fused benzene ring and (b) 1 molar equivalent of a compound selected from 3-chlorobenz[d]isothiazole-1,1-dioxide and 3-chloronaphtho[1,8-de]-1,2-thiazine-1,1-dioxide in a suitable inert organic solvent to give (c) the compound having the formula

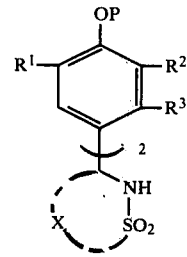

wherein P, R$^1$, R$^2$ and R$^3$ have the same meaning given above and X represents the atoms necessary to complete 2,3-dihydrobenz[d]isothiazole-1,1-dioxide or 2,3-dihydronaphtho[1,8-de]-1,2-thiazine-1,1-dioxide, said reaction being conducted at a temperature below about 0° C. when said G is Li and being conducted at a temperature above about 0° C. when said G is MgCl, MgBr or MgI.

Usually, the alkyl and alkoxy substituents comprising R$^1$, R$^2$ and R$^3$ are lower alkyl having 1 to 4 carbon atoms, such as, methyl, ethyl, n-propyl, isopropyl, and n-butyl and lower alkoxy having 1 to 4 carbon atoms, such as, methoxy, ethoxy, propoxy and butoxy.

In a particularly preferred embodiment, X represents the atoms necessary to complete 2,3-dihydrobenz[d]isothiazole-1,1-dioxide.

In a preferred embodiment, the compounds of the present invention may be represented by the formula

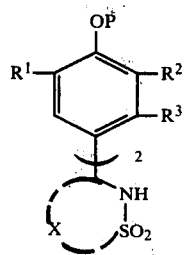

wherein P is a protecting group, R$^1$ and R$^2$ each are selected from hydrogen, alkyl, alkoxy, chloro and fluoro; R$^3$ is hydrogen, alkyl, alkoxy, or —OP; R$^2$ and R$^3$ taken together represent the carbon atoms necessary to complete a fused benzene ring; and X represents the atoms necessary to complete 2,3-dihydrobenz[d]isothiazole-1,1-dioxide or 2,3-dihydronaphtho[1,8-de]-1,2-thiazine-1,1-dioxide.

Specific examples of compounds of the present invention include

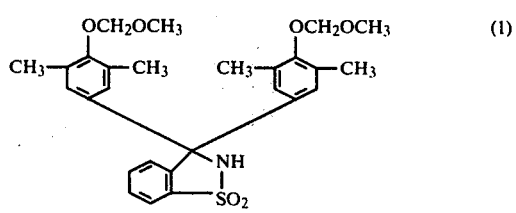
(1)

-continued
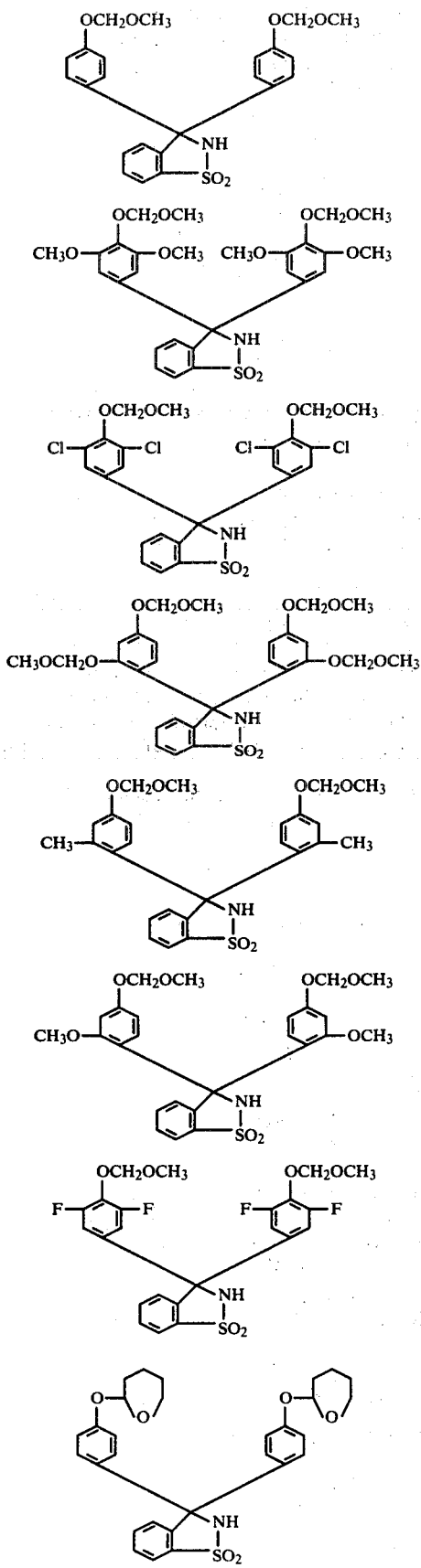
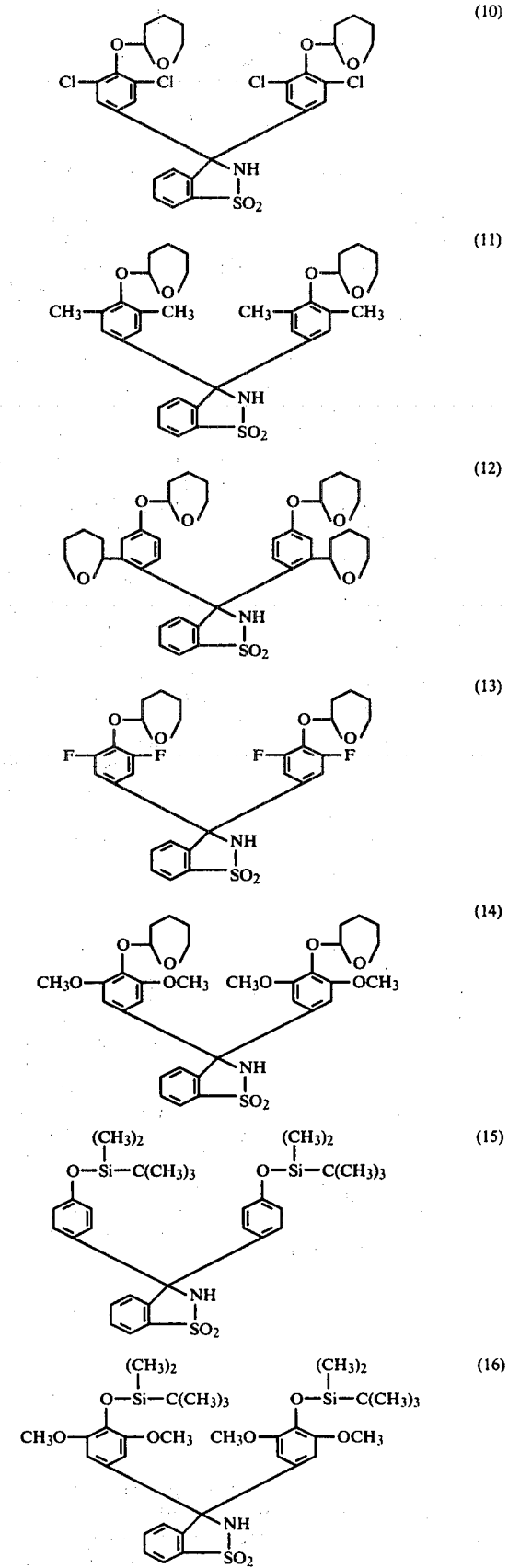

-continued

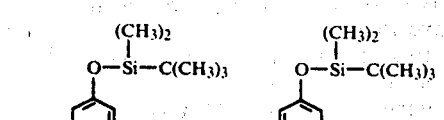 (17)

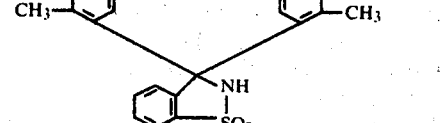 (18)

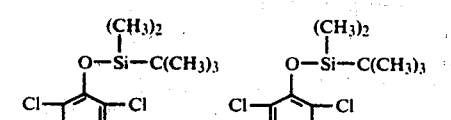 (19)

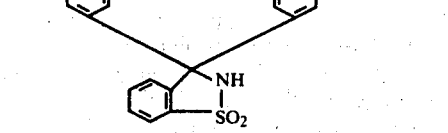 (20)

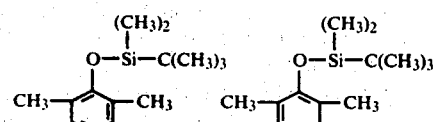 (21)

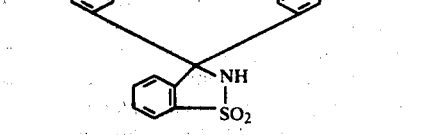 (22)

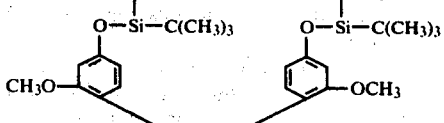 (23)

-continued

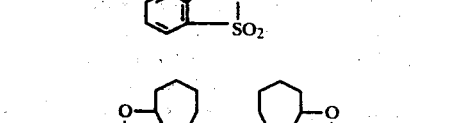 (24)

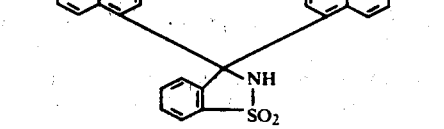 (25)

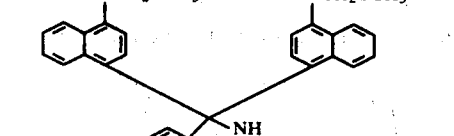 (26)

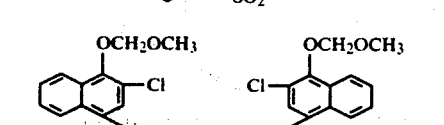 (27)

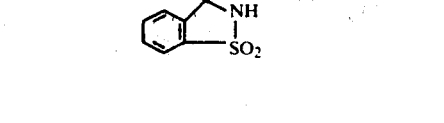 (28)

The starting phenols and 1-naphthols are prepared by blocking the functional hydroxy group and any substituent group(s), as may be appropriate, and then converting the blocked phenol or 1-naphthol to the corresponding Grignard or lithium reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange reaction using, for example, n-butyllithium. In preparing the Grignard reagent by reacting the blocked phenol or 1-naphthol with magnesium metal, the 4-halo substituent may be chloro, bromo or iodo.

The lithium reagent or Grignard reagent thus prepared is reacted with 3-chlorobenz[d]isothiazole-1,1-dioxide or 3-chloronaphtho[1,8-de]-1,2-thiazine-1,1-dioxide in an inert organic solvent. Any of the solvents ordinarily used with these organometallic reagents may be employed. Suitable solvents for use with both the lithium and Grignard reagents are ethers, such as, ethyl ether, dioxane and tetrahydrofuran. With the lithium reagent, hydrocarbon solvents, e.g., benzene, hexane, toluene and petroleum ether also are useful. When a lithium reagent is employed, the reaction temperature may vary over a relatively wide range from about −80° C. to 0° C. as may be readily determined for the particular reactants. For achieving maximum yields, the reaction generally is conducted at a temperature between about −65° and −25° C. When a Grignard reagent is employed, the reaction temperature may vary between about 0° and 50° C. and usually ranges between about 20° and 50° C. Though two molar equivalents of the Grignard or lithium reagent may be reacted with one molar equivalent of the saccharin pseudo-chloride, the Grignard or lithium reagent usually is employed in a slight excess of about 0.1 mole.

The groups selected for protecting the functional phenolic and naphtholic hydroxy group and other hydroxy groups that may be present in the phenol or 1-naphthol should be stable to and compatible with organolithium and Grignard reagents and should protect the hydroxy group(s) against reaction under the conditions encountered in the subject method and in the subsequent steps in the synthesis of the aforementioned N-acylated sulfam(na)phthalein products. In addition, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the phenol or 1-naphthol preferably is protected with methoxymethyl, 2-tetrahydropyranyl or dimethyl-t-butylsilyl. The blocked phenols and 1-naphthols employing these protecting groups may be prepared by methoxymethylation as described, for example, by Kaoru Fuji et al, *Synthesis*, 4, pp. 276–277 (1975), by tetrahydropyranylation as described, for example, by William E. Parham et al, *J. Amer. Chem. Soc.*, 70, pp. 4187–4189 (1948) or by silylating with dimethyl-t-butyl-silyl chloride in the presence of imidazole as described by E. J. Corey et al, *J. Amer. Chem. Soc.*, 94, pp. 6190–6191 (1972).

Depending upon the particular substituents that may be present in the blocked phenols (or 1-naphthols), it may be desirable to protect the substituent group(s) by selecting a protecting group that will render the substituent(s) compatible with organometallic reagents and yet be removable under weakly acid conditions together with the protecting group selected for the functional —OH to give the final product. As noted above, hydroxy groups in addition to the functional —OH of the phenol and 1-naphthol may be blocked simultaneously with the functional hydroxy group, for example, by tetrahydropyranylation or methoxymethylation. Groups other than hydroxy that should be protected may be blocked prior to or subsequent to the blocking of the functional —OH. For example, carboxy group(s) may be protected by reacting a carboxy-substituted 4-halophenol (or 4-halo-1-naphthol) with 2-amino-2-methyl-1-propanol followed by blocking of the functional —OH. Sulfonamido (—NH—SO$_2$—R°) and sulfamoyl (—SO$_2$—NH—R°) substituents may be protected by a t-butyl group.

As mentioned previously, the compounds provided by the subject method are useful as starting materials in the method disclosed and claimed in aforementioned copending application Ser. No. 836,010 which, for convenience, is incorporated herein. As discussed therein, 3,3-di(4'-OP-1'-phenyl/4'-OP-1'-naphthyl)-2,3-dihydrobenz[d]isothiazole-1,1-dioxides prepared as described above are reacted with a carboxylic acid halide in pyridine to give the corresponding N-acylated compound. About 1 to 2 moles of acid halide are used for each mole of the isothiazole-1,1-dioxide. Since the reaction is exothermic, external heating may not be necessary, but the reaction mixture may be heated to facilitate completion of the reaction, if desired. Ordinarily, the reaction temperature ranges between about 0° and 100° C., and preferably, the reaction is conducted in an inert atmosphere, for example, under nitrogen.

Optionally, the acylation step may be carried out by first reacting the isothiazole-1,1-dioxide with an equimolar amount or slight excess of an alkali metal hydride, MH, wherein M is sodium, potassium or lithium at 0° to 100° C. in an inert atmosphere, and then reacting the N-alkali metal salt thus formed with the carboxylic acid halide. Usually the acid halide is added to the reaction mixture containing the N-alkali metal salt. However, the N-alkali metal salt may be isolated prior to reaction with the acid halide, if desired. Solvents suitable for use in the alternate method of forming the N-acylated compound include dioxane, tetrahydrofuran, ethylether and benzene. The alkali metal, like the pyridine, affords substitution of the ring nitrogen of the isothiazole moiety in the acylation reaction.

Carboxylic acid halides are well known and may be prepared in a conventional manner, for example, by reacting the selected carboxylic acid, RCOOH, with phosphorus trichloride, phosphorus pentachloride or thionyl chloride to give the corresponding RCOCl, or by reacting the selected ROH with phosgene to give the corresponding ClCOOR.

Subsequent to the acylation step, the protecting group P is removed from the functional —OH by treating with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above. As indicated previously, any other protecting groups that may be present are removed simultaneously with the protecting group on the functional —OH.

The following examples are given to further illustrate the present invention and are not intended to limit the scope thereof.

EXAMPLE 1

Preparation of the compound having the formula

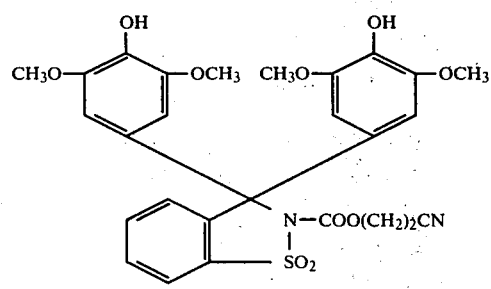

(a) 55 g. of 4-bromo-2,6-dimethoxy-methylenemethoxyphenyl ether was dissolved in 300 ml. of anhydrous tetrahydrofuran under a stream of nitrogen. The solution was cooled to −65° C. during which time some of the phenyl ether precipitated. To this was added 79 ml. of butyl-lithium (2.4 M in hexane) at a range to keep the temperature below −50° C. The resulting solution was cooled to −65° C. and was stirred for 30 minutes. To this solution was added 19 g. of saccharin pseudo-chloride in two portions so as to keep the temperature below −40° C. The reaction solution was cooled to −65° C. and was stirred for 40 minutes. TLC showed one main spot on silica gel with 10 ml. ether/2 drops methanol. The reaction solution was poured into 2000 ml. of water and made acidic to pH 6. The mixture was extracted two times with ether (2 liters) and the ether washed with water. The ether was dried over sodium sulfate and evaporated to leave a light yellow solid. The solid was recrystallized from 450 ml. of n-propanol to give 42 g. of 3,3-di(3',5'-dimethoxy-4'-methoxymethoxy-1'-phenyl)-2,3-dihydrobenz[d]isothiazole-1,1-dioxide as off-white crystals (melting range 151.5°–152.5° C.).

(b) The compound prepared in step (a) (27.0 g.) was dissolved in 125 ml. of dioxane at room temperature under nitrogen. To this solution was added 2.50 g. of NaH (57% oil dispersion) and the resulting dispersion stirred for 45 minutes. (Evolution of hydrogen was observed.) Then 8.0 ml. of ClCOOCH$_2$CH$_2$CN was added and an exotherm resulted. The resulting reaction mixture was stirred for 3 hours. The initial yellow color disappeared and a white dispersion formed. The dispersion was poured into 2 liters of water, made neutral with dilute HCl and extracted with chloroform. The chloroform was washed with water, separated, dried over sodium sulfate, and evaporated to yield a white solid. The solid was stirred with ethyl ether, isolated by filtration, dried in vacuo, and crystallized from methanol. The white needles that formed were recovered by filtration to give the

derivative of 3,3-di(3',5'-dimethoxy-4'-methoxymethoxy-1'-phenyl)-2,3-dihydrobenz[d]isothiazole-1,1-dioxide.

(c) 3.7 g. of 3,3-di(3',5'-dimethoxy-4'-methoxymethoxy-1'-phenyl)-2-(β-cyanocarbethoxy)-2,3-dihydrobenz[d]-isothiazole-1,1-dioxide prepared as in step (b) above was placed in 200 ml. of methanol and 2 drops of HCl were added. The resulting solution was refluxed and the reaction was followed by TLC on silica gel with ether. When TLC indicated that no more blocked compound remained, the reaction was discontinued and the methanol removed in vacuo to leave an egg-white solid (3.2 g.). This was dissolved in 80 ml. of 1,2-dichloroethane with heating and 80 ml. of petroleum ether was added with swirling. The solution was cooled and the light beige crystals that formed were collected and dissolved in 175 ml. of ethanol at reflux. The ethanol solution was allowed to cool in the refrigerator overnight and 2.7 g. of the title compound was collected as white needles (melting range 191°–193° C.).

The methoxymethylation of 4-bromo-2,6-dimethoxyphenol was carried out as follows:

To a 3 liter flask was added 300 g. of P$_2$O$_5$ under nitrogen and 800 ml. of chloroform (previously dried over P$_2$O$_5$). The mixture was cooled to −15° C. with a dry-ice acetone bath and then 50 g. of 4-bromo-2,6-dimethoxyphenol in 800 ml. of dimethoxymethane was added over a 25 minute period while maintaining the temperature at −15° C. or below. To the resulting reaction mixture was added 1 ml. of conc. sulfuric acid and then the temperature was allowed to come to room temperature. During this time, a tacky mass of P$_2$O$_5$ developed. The reaction mixture was stirred for 3 hours. TLC indicated that the reaction was complete. The chloroform was then decanted into 400 ml. of 10% aqueous sodium hydroxide, stirred well and the chloroform layer separated, washed with water, dried over Na$_2$SO$_4$ and evaporated to leave light tan crystals. n-Propanol was added to the crystalline residue, stirred and filtered to give 32.7 g. of the title compound as white crystals (melting range 98°–100° C.).

Saccharin pseudo-chloride was prepared as follows:

35 g. of saccharin and 43.7 g. of PCl$_5$ were heated at 170° C. for 1½ hours during which time complete solution occurred and POCl$_3$ began to reflux. The POCl$_3$ was removed at reduced pressure to leave a crystalline residue. Diethyl ether was added to the crystalline residue and stirred well. The title compound was recovered as white crystals, 12.5 g. (melting range 146°–147° C.).

EXAMPLES 2–4

The compounds having the formulas

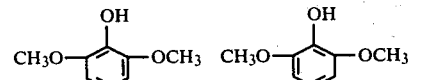

Example 2

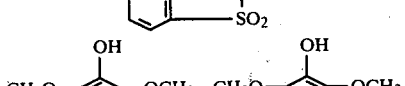

Example 3

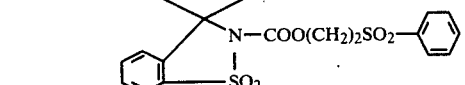

Example 4 were prepared in the same manner described in Example 1 except that the acylating agents employed were

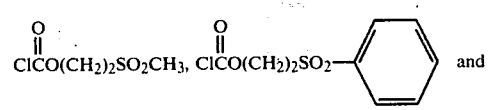

and

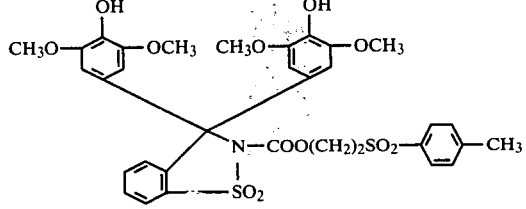

-continued

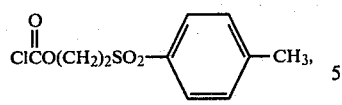

respectively,

EXAMPLE 5

Preparation of the compound having the formula:

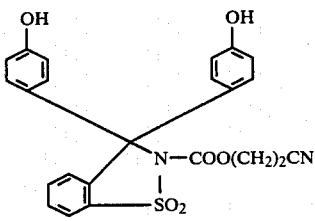

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudo-chloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

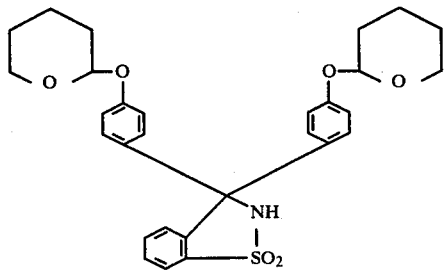

(b) Compound A as prepared in step (a) (10.0 g.) was placed in 100 ml. of dioxane and 0.88 g. of sodium hydride (as 57% oil dispersion) was added at room temperature under nitrogen (hydrogen evolution was observed). The resultant mixture comprising the N-sodium salt of the above compound was stirred 1 hour and then 2.4 ml. of ClCOOCH2CH2CN was added. A white precipitate formed immediately. The reaction mixture was stirred overnight, then poured into 200 ml. water. The aqueous mixture was extracted with three 250 ml. portions of ether, which were combined and dried over sodium sulfate. The ether was removed in vacuo and the resulting solid washed with petroleum ether. Upon drying, 10.5 g. of the crude N-acylated derivative was obtained. The N-acylated compound has the formula (c) Compound B (5.0 g.) as prepared in step (b) was dissolved in 50 ml. of warm methanol which contained two drops of conc. HCl. This solution was allowed to stand at room temperature for 30 min. at which time the analysis indicated both tetrahydropyranyl protecting groups had been removed. The methanol and HCl were removed in vacuo leaving 5.0 g. of a light yellow solid which was fractionated via column chromatography (silica gel; ether) to give a pure sample of the title compound.

Tetrahydropyranylation of p-bromo-phenol used in the preparation of compound A was carried out as follows:

To 10.5 ml. of dihydropyran containing 2 drops of conc. HCl was added 10.0 g. of p-bromophenol. (The reaction was exothermic; temperature rose to 35° C.). After the addition was completed, the colorless solution obtained was heated to 50° C. and allowed to cool with stirring for 1 hour. The solution was extracted with 20 ml. of ether and 10 ml. of 10% NaOH. The ether layer was dried over anhydrous Na2SO4 and evaporated under reduced pressure to leave an oil. 80 ml. of ethanol was added to the oil and the resulting ethanol solution was allowed to stand. The white crystals that formed were recovered by filtration and dried under vacuum to yield 7.3 g. of the blocked phenol. The mother liquor was concentrated to one-half its original volume and cooled. More crystals formed which were isolated to yield an additional 2.1 g. of blocked phenol.

EXAMPLE 6

Preparation of the compound having the formula:

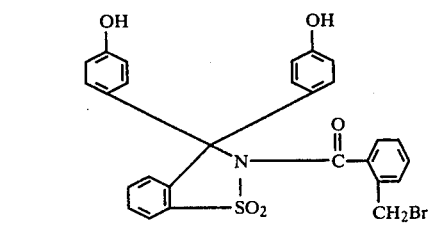

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudo-chloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

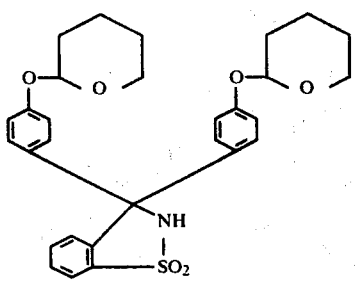

(b) 1.0 g. of the compound prepared in step (a) was placed in 15 ml. of dioxane and 0.08 g. of sodium hydride (as 57% oil dispersion) was added at room temperature under nitrogen. (Hydrogen evaluation was observed.) The resultant mixture comprising the N-sodium salt of the above compound was stirred 1 hour and then 0.342 g. of

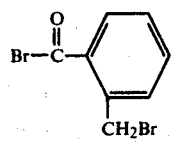

was added. A white precipitate formed immediately. The reaction mixture was stirred overnight, then poured into 100 ml. water. The white precipitate that formed was filtered, extracted with diethyl ether giving a yellow glass that was refluxed in ligroin (90°-100° C. boiling range). The ligroin was decanted leaving a solid comprising the N-acylated derivative of the above compound wherein the acyl group is

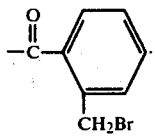

(c) To remove the 2'-tetrahydropyranyl protecting groups and obtain the product, 20 mls. of 10% HCl solution was added to the solid and the orange solid obtained was filtered and dried. A second crop of precipitate was recovered from the water precipitation which was filtered and treated with 10% HCl to give an additional 0.5 g. of solid. The solids were combined and fractionated via preparative TLC (silica gel/ether) to give a pure sample of the title compound.

EXAMPLE 7

Preparation of the compound having the formula

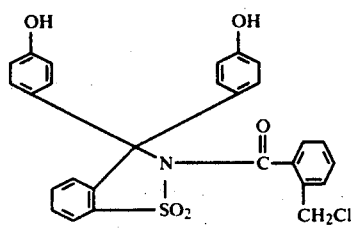

The title compound was prepared according to the procedure of Example 6 except that

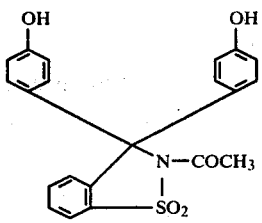

was employed as the acylating agent in step (b).

EXAMPLE 8

Preparation of the compound having the formula

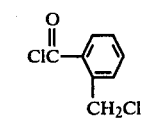

(a) 9.5 g. of p-bromoanisole in 20 ml. of dry tetrahydrofuran was added dropwise to 1.2 g. of magnesium turnings in 20 ml. of tetrahydrofuran. An $I_2$ crystal was added, and the mixture was heated to reflux. After refluxing for 1 hour, the mixture was cooled, and 5.0 g. of saccharin pseudo-chloride was added portionwise. An exotherm was observed. The reaction mixture was refluxed for 1 hour. 100 ml. of water was added followed by dilute HCl until pH 5. The mixture was then extracted with ether. The ether was dried and evaporated to leave a yellow residue. The residue was dissolved in 200 ml. of methanol and 2.0 g. of carbon black was added. The methanol solution was filtered and evaporated to leave a light yellow solid which was vacuum dried to give 8.5 g. of 3,3-di(4'-methoxy-1'-phenyl)-2,3-dihydrobenz[d]isothiazole-1,1-dioxide.

(b) 1.0 g. of the compound prepared in step (a) was dissolved in 20 ml. of dry dioxane. To this was added 0.12 g. of NaH as a 57% oil dispersion, and the solution was stirred until hydrogen evolution ceased. Additional NaH dispersion was added portionwise until no more hydrogen was evolved (about 0.05 g.). The solution was stirred for 1 hour, and 0.20 ml. of acetyl chloride was added. The temperature rose from 22° C. to 27.5° C. Stirring was continued for 3 hours at room temperature and then 200 ml. of water was slowly added. The white solid that formed was filtered, washed with water and dissolved in ether. The ether was extracted with 0.5 N NaOH, dried and evaporated to give 0.6 g. of 2-(acetyl)-3,3-di(4'-methoxy-1'-phenyl)-2,3-dihydrobenz[d]isothiazole-1,1-dioxide as a white solid.

(c) 0.5 g. of the compound prepared in step (b) was dissolved in 20 ml. of dichloromethane, cooled to −70° C. and a solution of 0.5 ml. of boron tribromide in 10 ml. of dichloromethane was added drowise. An immediate red color formed. After addition was complete (about 10 minutes), the solution was allowed to reach room temperature, then refluxed for 3 hours and then stirred at room temperature overnight. Water was added and the dichloromethane layer was isolated, dried over sodium sulfate and evaporated to give a solid residue. The solid was extracted with ether; the ether solution was filtered and evaporated after drying to yield a pink solid (0.45 g.). The solid was dissolved in 0.5 N potassium hydroxide, extracted with ether and then the water solution was reacidified with acetic acid. The solid that formed was extracted with ether and the ether dried and evaporated to yield the title compound as an egg-white solid.

EXAMPLES 9 AND 10

Preparation of the compounds having the formulae:

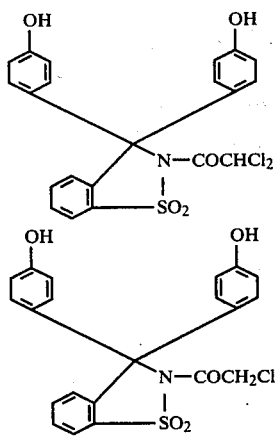

(a) 2'-tetrahydropyranyl 4-bromophenyl ether (9.0 g.) in 20 ml. of tetrahydrofuran was added dropwise to 0.85 g. of magnesium in 20 ml. of tetrahydrofuran under nitrogen. After addition was complete, the dispersion was refluxed for 2 hours and then saccharin pseudo-chloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

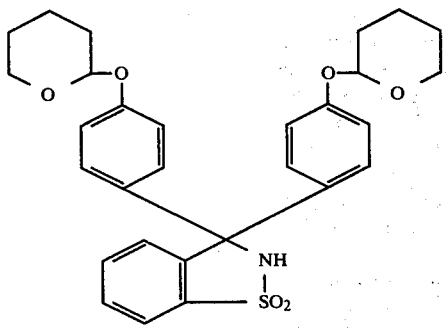

The compound prepared in step (a) was sequentially reacted with NaH and the appropriate acylating agents, namely,

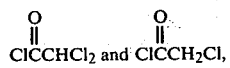

respectively, as described in step (b) of Example 8 and then the protecting groups were removed by treating the N-acylated compounds with 10% HCl solution to yield the title compounds.

EXAMPLE 11

Preparation of the compound having the formula:

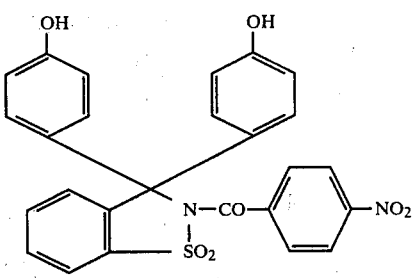

The title compound was prepared according to the procedure described in Examples 9 and 10 above except that the acylating agent employed was

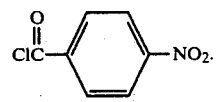

EXAMPLE 12

The compound having the formula

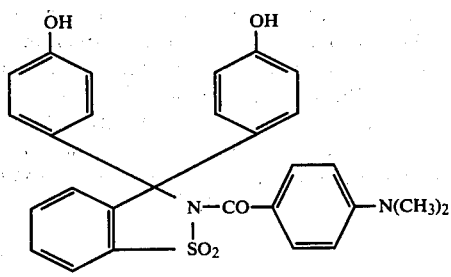

was prepared according to the procedure described in Examples 9 and 10 except that the acylating agent employed was

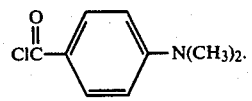

EXAMPLE 13

Preparation of the compound having the formula:

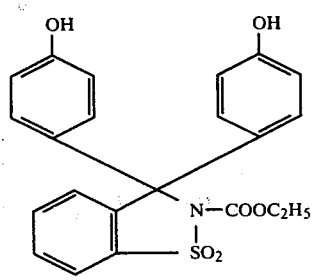

(a) 2'-tetrahydropyranyl 4-bromophenyl ether (9.0 g.) in 20 ml. of tetrahydrofuran was added dropwise to 0.85 g.

of magnesium in 20 ml. of tetrahydrofuran under nitrogen. After addition was complete, the dispersion was refluxed for 2 hours and then saccharin pseudo-chloride (3.5 g.) was added portionwise. An exotherm was observed, and the green solution that formed turned yellow-brown. The reaction solution was stirred overnight and then slowly added to 500 ml. of water. The precipitate that formed was slowly filtered and the solid obtained was dissolved in ether, dried and evaporated to yield 8.5 g. of light yellow solid having the formula:

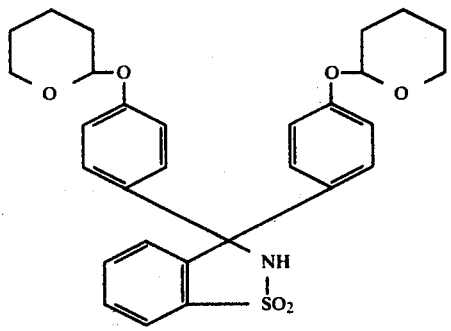

(b) The compound as prepared in step (a) (1.0 g.) was placed in 10 ml. of dioxane and 0.08 g. of sodium hydride (as 57% oil dispersion) was added at room temperature under nitrogen. (Hydrogen evolution was slow.) The solution went from light yellow to greenish then to yellow. The reaction was accelerated by heating to about 50° C. and then allowing the solution to cool to room temperature, about 1 hour. To the resulting solution comprising the N-sodium salt of Compound A was added 0.18 ml. of ethylchloroformate and the reaction mixture was stirred over the weekend.

(c) To remove the protecting groups, the solution was poured into 20 ml. of conc. HCl. After stirring for 15 minutes, the solution went from pink-red to brown. The precipitate that formed was filtered and dried under vacuum. Crystallization from 1:1 methanol-water gave 0.5 g. of the title compound as a white solid.

EXAMPLES 14 AND 15

Preparation of the compounds having the formulae:

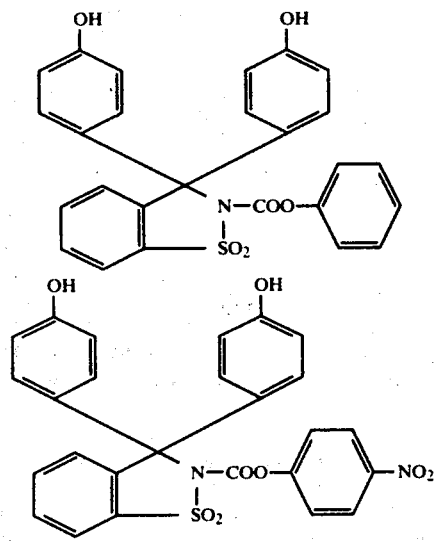

The title compounds were prepared according to the procedure described in Example 13 above except that the acylating agents employed in step (b) were

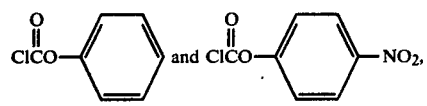

respectively.

EXAMPLE 16

Preparation of the compound having the formula:

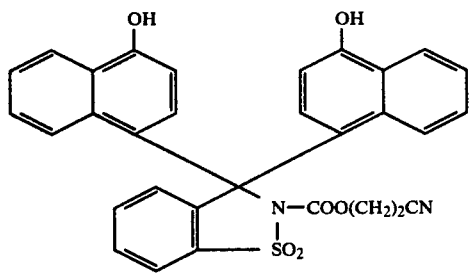

(a) To a solution of 168 mg. of t-potassium butoxide in 5 ml. of dry tetrahydrofuran was added 834 mg. of 3,3-di[4'-(2''-tetrahydropyranyloxy)-1'-naphthyl]-2,3-dihydrobenz[d]isothiazole-1,1-dioxide in several small portions under nitrogen. The yellow-brown solution obtained was stirred for 2 hours at room temperature and then cooled to an ice bath.

(b) To the cooled solution of step (a) was added dropwise 267 mg. of β-cyanoethylchloroformate. (The color changed to light yellow.) The resulting solution was stirred over the weekend at room temperature under nitrogen during which time most of the solvent had evaporated leaving yellow-orange solids comprising the title compound and deblocked starting material.

(c) The yellow-orange solids were taken up in 25 ml. of ether and the ether solution concentrated to about 10 ml. The crystals that formed were filtered, washed with ether and the orange and yellow components separated by preparative TLC on (silica gel/ether). The orange component was removed by eluting with n-butanol and the yellow component was removed by eluting with methanol. The methanol was then evaporated to give the title compound.

The intermediate having the formula

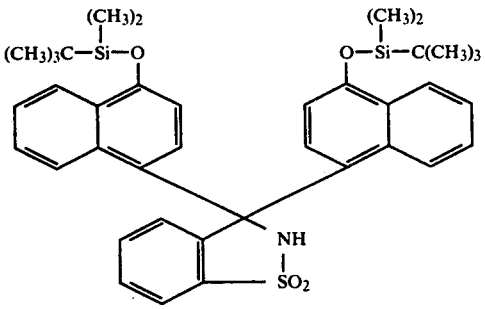

was prepared as follows:
(a) 16.87 g. of 4-bromonaphthyl dimethyl-t-butylsilyl ether was dissolved in 60 ml. of anhydrous ethyl ether under nitrogen, and the solution then cooled to −60° C. in a dry ice-acetone bath. 20.8 ml. of 2.4 N n-butyllithium in hexane was added to the cooled solution dropwise over a period of 15–20 minutes. The reaction mixture was stirred for 30 minutes and allowed to come to 15° C. over 45 minutes.

(b) The solution of step (a) was then cooled back to −40° C., and 4.63 g. of saccharin pseudo-chloride was added portionwise. After addition was complete, the reaction mixture was allowed to warm to room temperature, stirred at room temperature overnight and cooled. 50 ml. of cold water was added followed by the addition of dilute HCl until the pH reached 3–4. The ether phase was separated, and the aqueous phase was extracted with 50 ml. of ether. The ether portions were combined, washed with 100 ml. of water, dried over sodium sulfate, filtered and evaporated under reduced pressure. The residue was dissolved in iso-propanol and the iso-propanol solution slowly poured into 1 liter aqueous HCl solution having a pH of 3. The aquous phase was decanted leaving a gummy residue. Treatment of the residue with iso-propanol and aqueous HCl (pH 3) was repeated and the final residue was dissolved in 250 ml. of iso-propanol. 3% HCl was added until precipitation ceased. The solution was allowed to stand for 10 min., the solvent decanted and water added to the gummy precipitate which on standing became crystalline. The precipitate was filtered and air-dried over the weekend to give 15.55 g. of the title compound.

The dimethyl-t-butylsilyl ether of 4-bromo-1-naphthol was prepared as follows:

4-Bromo-1-naphthol (22.1 g.) and dimethyl-t-butylsilyl chloride (18.1 g.) were dissolved in 50 ml. of dimethylformamide at room temperature. The resulting solution was cooled in an ice bath and imidazole (17.0 g.) added under nitrogen. (A slight exotherm was observed.) A solid precipitated and the reaction mixture was stirred overnight.

A small sample of the crude product was treated with water adjusted to a pH of about 4–5 with dilute HCl and the solids isolated and dried. TLC on silica gel using hexane showed the product but no starting material.

The reaction mixture remaining was poured into 1500 ml. of water at about 20° C. with stirring. The pH was adjusted to 4–5 with dilute HCl, and the solids were filtered, washed with water, and air-dried for 2 hours and dissolved in 150 ml. of boiling isopropanol. The isopropanol solution was filtered while hot and then cooled slowly to room temperature. Crystals began to form and after standing at room temperature overnight, the solution was cooled in an ice water bath for 1 hour and filtered. The solid collected was washed with small amounts of isopropanol, air-dried briefly and then dried in vacuo for 2 hours to give 24.3 g. of the title compound (melting range 70°–73° C.).

The 3,3-di[4′-(2″-tetrahydropyranyloxy)-1′-phenyl]-2,3-dihydrobenz[d]isothiazole-1,1-dioxide having the formula

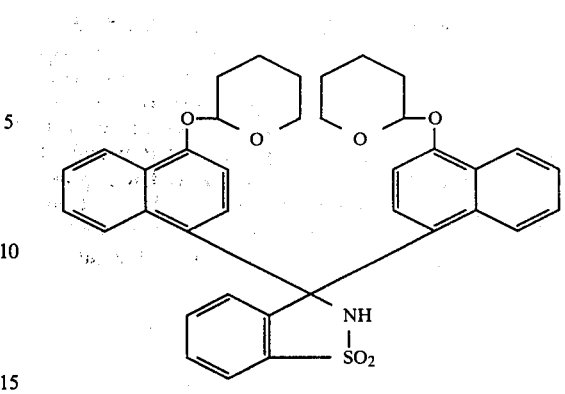

was prepared in the same manner as the foregoing intermediate.

The methoxymethyl ether and 2′-tetrahydropyranyl ether of 4-bromo-1-naphthol were prepared according to the procedures described above and the methoxymethyl and 2′-tetrahydropyranyl ethers of 4-bromo-1-naphthol were converted to the corresponding 4-lithium derivatives by reaction with n-butyllithium according to the procedures described above.

Where it is desired to prepare sulfamnaphthaleins, 3-chloronaphtho[1,8-de]-1,2-thiazine-1,1-dioxide may be substituted for the saccharin pseudo-chloride used in the foregoing Examples to give the corresponding sulfamnaphthalein intermediates and products. The pseudo-chloride of 2,3-dihydro-3-oxo-naphtho[1,8-de]-1,2-thiazine-1,1-dioxide may be prepared by reacting the 3-oxo-thiazine with PCl$_5$ as described above for the preparation of saccharin pseudo-chloride.

As mentioned above, the compounds of the present invention are useful as intermediates in the synthesis of certain 3,3-disubstituted-2,3-dihydrobenz[d]isothiazole-1,1-dioxides possessing a carbonyl group in the 2-position. Such compounds possessing a 4′-hydroxyphenyl moiety as one of the 3,3 substituents and a phenyl/naphthyl or 4′-substituted phenyl/4′-substituted naphthyl moiety as the other of the 3,3 substituents form the subject matter of copending U.S. Patent Application Ser. No. 836,021 of Stanley M. Bloom, Alan L. Borror and James W. Foley filed concurrently herewith, now U.S. Pat. No. 4,204,061, and of copending U.S. Patent Application Ser. Nos. 835,998; 836,005 and 836,009 of Alan L. Borror and James W. Foley also filed concurrently herewith. As discussed in the aforementioned applications, compounds may be selected for use as classical pH-sensitive indicator dyes or as photographic optical filter agents and filter agent precursors depending upon the 2-substituent of the benz[d]isothiazole ring. The photographic use of certain of the compounds as photographic optical filter agents and filter agent precursors forms the subject matter of copending U.S. Patent Application Ser. No. 836,006 of Stanley M. Bloom, Alan L. Borror and James W. Foley filed concurrently herewith, now U.S. Pat. No. 4,139,381. The 2,3-dihydrobenz[d]-isothiazole-1,1-dioxides possessing a 4′-hydroxynaphthyl moiety as one of the 3,3 substituents and a naphthyl or 4′-substituted naphthyl moiety as the other of the 3,3 substituents form the subject matter of copending U.S. Patent Application Ser. No. 836,067 of Alan L. Borror, Louis Cincotta, Ernest W. Ellis and James W. Foley filed concurrently herewith, now U.S. Pat. No. 4,195,180, and as described therein, compounds may be selected for use as classical pH-sensitive indicator dyes or as antihalo dyes in photography.

Since certain changes may be made in the above processes and products without departing from the scope of the invention herein involved, it is intended that all matter contained in the above description shall be interpreted as illustrative and not in a limiting sense.

We claim:

1. A process which comprises reacting (a) at least 2 molar equivalents of a compound having the formula

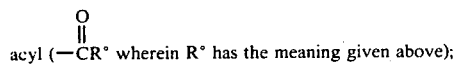

acyl (—CR° wherein R° has the meaning given above);

wherein G is Li, MgCl, MgBr or MgI; P is a protecting group selected from 2'-tetrahydropyranyl, methoxymethyl and dimethyl-t-butylsilyl; $R^1$ and $R^2$ each are selected from hydrogen, alkyl, alkoxy, chloro and fluoro; $R^3$ is hydrogen, alkyl, alkoxy, or —OP wherein P has the same meaning given above; and $R^2$ and $R^3$ taken together represent the carbon atoms necessary to complete a fused benzene ring and (b) 1 molar equivalent of a compound selected from 3-chlorobenz[d]isothiazole-1,1-dioxide and 3-chloronaphtho-[1,8-de]-1,2-thiazine-1,1-dioxide in a suitable inert organic solvent to give (c) the compound having the formula

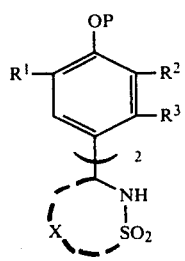

wherein P, $R^1$, $R^2$ and $R^3$ have the same meaning given above and X represents the atoms necessary to complete 2,3-dihydrobenz[d]isothiazole-1,1-dioxide or 2,3-dihydro-naphtho[1,8-de]-1,2-thiazine-1,1-dioxide, said reaction being conducted at a temperature below about 0° C. when said G is Li and being conducted at a temperature of above about 0° C. when said G is MgCl, MgBr or MgI.

2. A process as defined in claim 1 wherein said G is Li.

3. A process as defined in claim 1 wherein said G is MgCl, MgBr or MgI.

4. A process as defined in claim 1 wherein said (b) is 3-chlorobenz[d]isothiazole-1,1-dioxide.

5. A process as defined in claim 2 wherein said reaction is conducted at a temperature between about −80° C. and 0° C.

6. A process as defined in claim 3 wherein said reaction is conducted at a temperature between about 0° and 50° C.

7. A process as defined in claim 1 wherein $R^1$ and $R^2$ each are hydrogen.

8. A process as defined in claim 7 wherein $R^3$ is hydrogen.

9. A process as defined in claim 1 wherein $R^1$ and $R^2$ each are alkyl.

10. A process as defined in claim 9 wherein $R^3$ is hydrogen.

11. A process as defined in claim 1 wherein $R^1$ and $R^2$ each are alkoxy.

12. A process as defined in claim 11 wherein $R^3$ is hydrogen.

13. A process as defined in claim 1 wherein $R^2$ and $R^3$ taken together represent the carbon atoms necessary to complete a fused benzene ring.

14. A process as defined in claim 13 wherein $R^1$ is hydrogen.

15. A process as defined in claim 1 wherein said (a) is

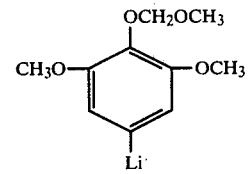

16. A process as defined in claim 1 wherein said (a) is

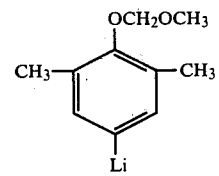

17. A process as defined in claim 1 wherein said (a) is

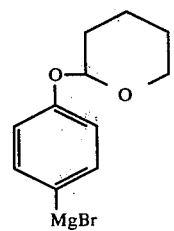

18. A process as defined in claim 1 wherein said (a) is

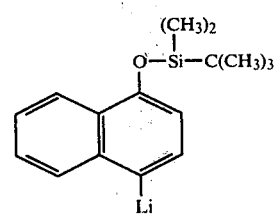

* * * * *